(12) United States Patent
Chowdry et al.

(10) Patent No.: US 8,990,250 B1
(45) Date of Patent: Mar. 24, 2015

(54) COHORT SELECTION WITH PRIVACY PROTECTION

(75) Inventors: Arnab Chowdry, Sunnyvale, CA (US); Alexander Kompel, Santa Clara, CA (US); Michael Polcari, San Francisco, CA (US)

(73) Assignee: 23andMe, Inc., Mountain View, CA (US)

( * ) Notice: Subject to any disclaimer, the term of this patent is extended or adjusted under 35 U.S.C. 154(b) by 305 days.

(21) Appl. No.: 13/270,429

(22) Filed: Oct. 11, 2011

(51) Int. Cl.
*G06F 17/30* (2006.01)

(52) U.S. Cl.
USPC ........................................ 707/781

(58) Field of Classification Search
None
See application file for complete search history.

(56) References Cited

U.S. PATENT DOCUMENTS

| | | | | |
|---|---|---|---|---|
| 8,464,046 B1* | 6/2013 | Kragh | | 713/156 |
| 2003/0188200 A1* | 10/2003 | Paquin et al. | | 713/202 |
| 2004/0133358 A1* | 7/2004 | Bryant et al. | | 702/19 |
| 2005/0176031 A1* | 8/2005 | Sears et al. | | 435/6 |
| 2005/0222981 A1* | 10/2005 | Lawrence et al. | | 707/3 |
| 2006/0047657 A1* | 3/2006 | Frieder et al. | | 707/9 |
| 2007/0244701 A1* | 10/2007 | Erlanger et al. | | 704/246 |
| 2010/0122083 A1* | 5/2010 | Gim et al. | | 713/162 |
| 2010/0169022 A1* | 7/2010 | Bangera et al. | | 702/19 |
| 2010/0287190 A1* | 11/2010 | Anderson | | 707/769 |
| 2012/0035954 A1* | 2/2012 | Yeskel | | 705/3 |

* cited by examiner

*Primary Examiner* — Syed Hasan
(74) *Attorney, Agent, or Firm* — Van Pelt, Yi & James LLP

(57) ABSTRACT

Assembling a cohort includes: receiving genetic characteristic information pertaining to a desired genetic characteristic; using the genetic characteristic information to search a data storage comprising information of previously genotyped individuals to derive a candidate group having the desired genetic characteristic; and assembling the cohort based at least in part on the candidate group.

16 Claims, 6 Drawing Sheets

COHORT SELECTION WITH PRIVACY PROTECTION

BACKGROUND OF THE INVENTION

Today, clinical research targeting specific genetic factors in human subjects is typically conducted by recruiting candidates that may have a certain genetic condition through special pools (e.g., patient groups), screening for the particular genotype that is being studied, and selecting subjects based on the screening results. The selection process tends to be difficult for several reasons. First, a large number of candidates often need to be recruited. Reaching out to these people, making them interested in the study, and getting them to sign up can be costly and time consuming. Second, all candidates have to be screened to determine whether they have the specific genetic condition, which is an expensive and laborious process. For studies of rare genetic conditions in particular, multiple iterations may be required to achieve a significant study population.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Assembling a cohort based at least in part on genetic information of previously genotyped individuals is disclosed. As used herein, a cohort refers to a group of individuals participating in a study such as a clinical trial, a disease investigation, genetic research, etc. Participants in a cohort are selected based on some criteria specified by those conducting the study. In some embodiments, personal information (e.g., individuals' genotype/phenotype information, family history, environmental information, etc.) and corresponding account information (e.g., name, contact information, social security number, etc., that pertain to individuals' real world identity) are stored separately, and role-based access control is enforced to provide privacy protection. In some embodiments, access is further restricted based on projects, such that users (such as researchers and investigators) associated with certain projects can only access information about individuals participating in the projects.

Figure 1:
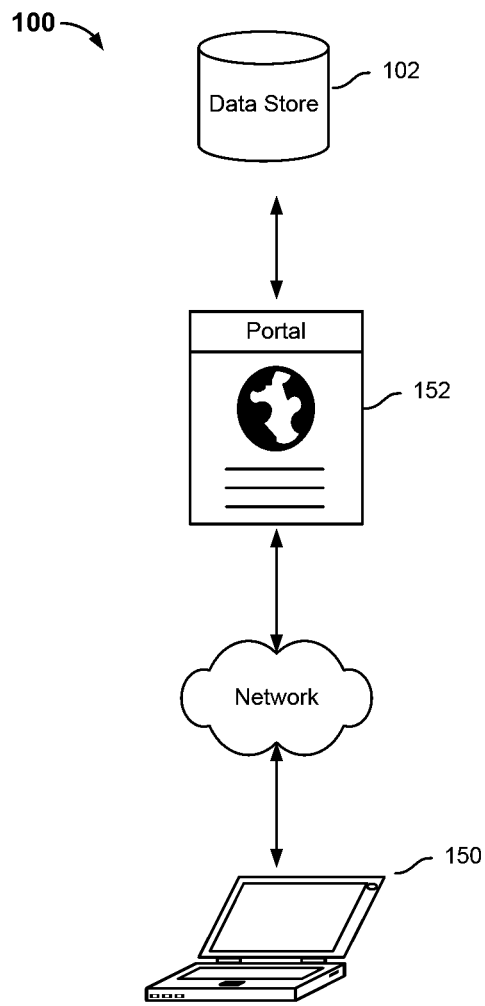
FIG. 1 is a block diagram illustrating an embodiment of a system configured for assembling a cohort.

FIG. 1 is a block diagram illustrating an embodiment of a system configured for assembling a cohort. In this example, system 100 is a web-based system, although other systems may also be used. System 100 includes a portal 152 and a data store 102. Client devices 150 access the cohort assembling service provided by system 100 via a client application such as a web browser. Client devices 150 may be a desktop computer, a laptop computer, a handheld/tablet device, a mobile/wireless device, or any other hardware/software combination that supports client applications. The client device may access the service via a network or directly. Various users of the system, such as researchers, investigators, administrators, etc., can access the portal and obtain information using their client devices.

Portal 152 provides client access and implements the cohort assembling functions. Portal 152 may be implemented using one or more servers or other hardware/software combinations. The portal has access to one or more data storages 102 (also referred to as data stores). In various embodiments, the data store may be implemented using a database, a file system, or any other appropriate data storage techniques. As will be described in greater detail below, the data store is configured to store account information and personal information pertaining to previously genotyped individuals. The personal information includes genetic information for the individuals and, optionally, phenotypic information, family history information, environmental information, etc. The genetic information in the data store may be collected through a personal genetic information service such as 23 and Me's Personal Genome Service®, where DNA samples (e.g., saliva) are collected from individuals and genotyped using DNA microarray or other appropriate techniques. In some embodiments, since the genetic information was not initially collected just for the purpose of a particular study pertaining to a specific gene, genomic information (e.g., full genetic information) of the individuals rather than specific genetic information (e.g., information pertaining to a particular gene) is obtained and stored. In various embodiments, full or partial genome sequences, exomes, single-nucleotide polymorphisms (SNPs) and/or other appropriate representations of the individuals' genomic information are stored in the data store.

In some embodiments, other health-related information not based on genotyping (such as phenotypic, family history, and environmental information) is also collected from the individuals and stored in the data store. For example, individuals can be asked to enter phenotypic information such as disease conditions, blood test results, liver panel test results, etc. They may also be asked to enter other related information such as age, ethnicity, personal habits that include exercise, diet, smoking, health conditions of relatives, and many other types of information that may be of interest. In some embodiments, both genotypic and non-genotypic information can be imported from other sources such as a patient record database or a different genetic information database.

Figure 2:
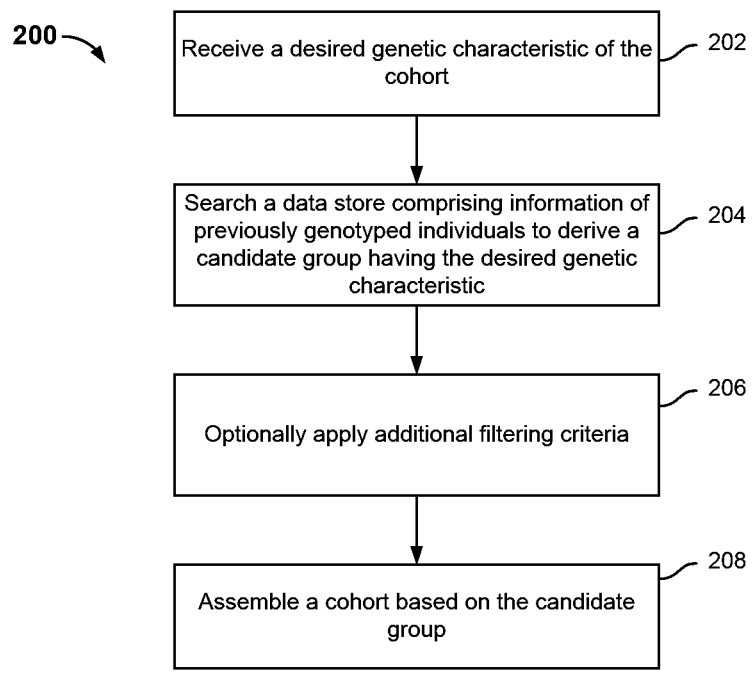
FIG. 2 is a flowchart illustrating an embodiment of a process for assembling a cohort.

FIG. 2 is a flowchart illustrating an embodiment of a process for assembling a cohort. Process 200 may be implemented on a system such as 100.

At 202, a desired genetic characteristic for the cohort is received. The desired genetic characteristic may include one or more genotypes, a particular haplogroup, etc. In some embodiments, the desired genetic characteristic is identified by researchers conducting the cohort study and entered into the system as an input. For example, in a study on Alzheimer's disease, the desired genetic characteristic is the presence of the APOE e4 genotype in a person's genome; in a study of Parkinson's disease, the desired genetic characteristic is the presence of the LRRK2 G2019S mutation in a person's genome. Additional genetic, phenotypic, and/or other types of personal information may also be indicated and received. For example, the researcher may indicate that the cohort should comprise individuals who are male, over the age of 45, and non-smoking.

At 204, the desired genetic characteristic information is searched in a data store comprising information of previously genotyped individuals to derive a candidate group having the genetic characteristic. Information about the desired genetic characteristic (e.g., a particular genotype and its presence/absence/variation in an individual's genome) and other indicated traits are transformed into a data store query to be processed by the system. For example, the data store may be queried for all individuals who have the APOE e4 gene, are male, over the age of 45, and non-smoking. These individuals are identified to form a candidate group. Comparing to existing techniques of specifically testing participants for the desired genetic characteristic and making a selection based on test results, using a data store comprising genomic information of previously genotyped individuals allows for better scalability since candidate groups can be identified much more quickly and easily. Preferably, the data store includes genomic information of more than 100,000 individuals so that a sufficiently large pool is available to derive a candidate group.

At 206, certain additional filtering criteria are optionally applied to the candidate group to make further selections.

In some embodiments, filtering criteria may be based on genomic information. For example, some studies may want candidates that are not related to each other by blood. While candidates will typically report immediate family members, they often do not report more distant relatives such as cousins that may also be among the candidates. Genomic information of the candidates is compared to determine their relatedness based on the amount of DNA shared. Various techniques for DNA-based relative identification may be used, such as the technique based on "Identical by Descent" (IBD) regions in the individuals' genome described in U.S. patent application Ser. No. 12/644,791 entitled FINDING RELATIVES IN A DATABASE, filed Dec. 22, 2009, which is incorporated herein by reference in its entirety for all purposes. Depending on the needs of the study, further filtering can be made to remove related people from the cohort, select only related people into the cohort, etc.

As another example, comparison of individuals' genomes with reference genomes of various races (e.g., European, African, Asian) can give indications of the individuals' race, since one's genome is likely to overlap more with the reference genome of his/her own race. Cohort selection for studies where race is a factor can be conducted based on the results of the comparisons, where individuals are selected into or excluded from the study based on the results.

Genome-based determination of relatedness, race, etc., tends to be more accurate than self-reported information and can be used alone or in conjunction with self-reported information to filter candidates and facilitate cohort selection.

In some embodiments, filtering criteria includes non-genetic information. For example, the candidates may be given a survey to identify additional information that is not already included in the data store, be subject to certain screening tests (e.g., the Montreal Cognitive Assessment (MoCA®) test) or laboratory tests, etc. Candidates that fulfill requirements based on the results can be subject to further selections or be admitted to the cohort.

At 208, the cohort is assembled based on the candidate group. Candidate information for the cohort members may be marked, copied, or otherwise indicated. In some embodiments, the candidate group is used to form an expanded cohort. For example, in some studies it is desirable to have more related people in the candidate pool (e.g., studies of rare genetic traits and/or family inheritance); thus, invitations to participate in the study can be extended to relatives of the candidate group to increase the cohort size.

Once a cohort is formed, based on the account information of the cohort members, investigators facilitating the research can contact the cohort members, administer clinical trials, record results, etc., and researchers conducting the research can review personal data (and later clinical data) of the cohort members. Preferably, measures are taken to protect the individuals' privacy and segregate the types of information researchers/investigators can access.

Figure 3:
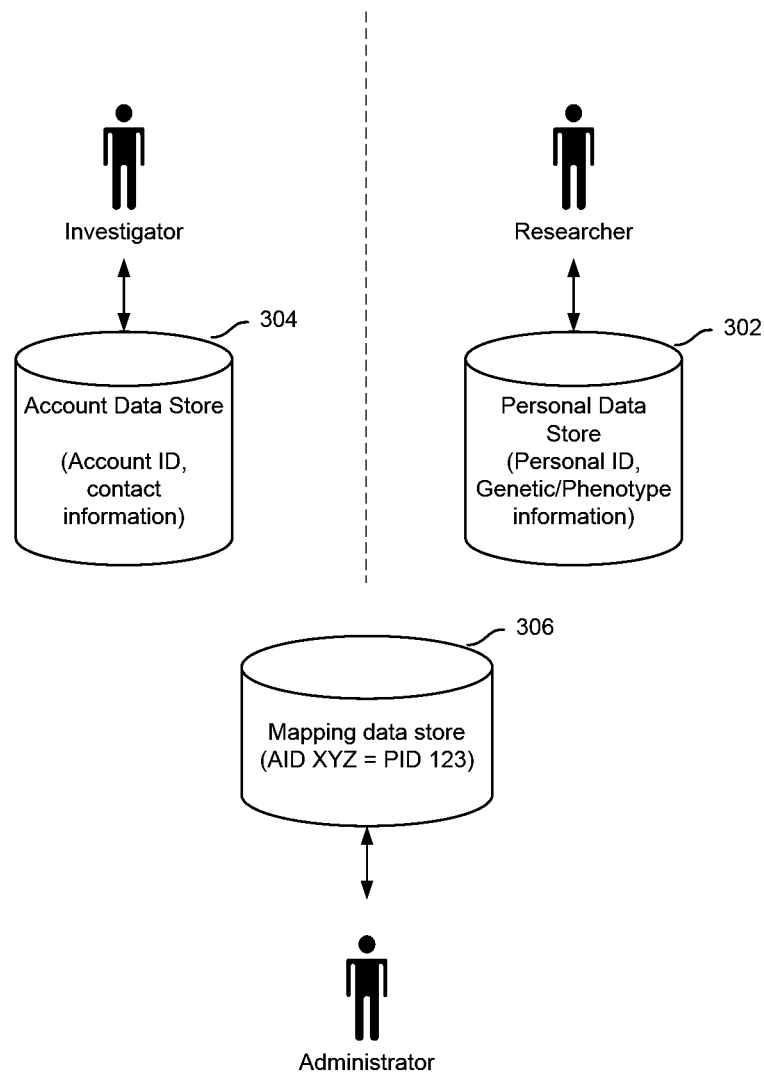
FIG. 3 is a data diagram illustrating an embodiment of data stores used in a cohort assembling system with privacy protection.

FIG. 3 is a data diagram illustrating an embodiment of data stores used in a cohort assembling system with privacy protection. In this example, data store 100 is implemented using separate data stores to anonymize personal information and account information, thus preventing the individuals' account information from being linked to their personal information. In other words, users of the system (e.g., researchers and investigators) are prevented from looking up the personal information of a particular individual based on the individual's name, address, or other contact information, or looking up the contact information of a particular individual based on the individual's genetic/phenotypic/other personal information.

As shown in the diagram, an account data store 304 is used to store account information associated with the previously genotyped individuals, such as contact information (e.g., names, street addresses, email/Internet accounts, phone numbers) that can be read and understood by a human. In this example, an individual is assigned a unique account identification (AID) that is linked to his/her account information. The AID can be used to look up the individual's account information. In some embodiments, the AID comprises a randomized number or string that does not relate to or reveal the real world identity of the individual.

A separate personal data store 302 is used to store personal information including genetic, phenotypic, and other related information. In this example, an individual is assigned a unique personal identification (PID) linked to his/her personal information in data store 302. The PID can be used to look up the individual's personal information. In some embodiments, the PID is a randomized number or string that does not relate or reveal the individual's real world identity.

The personal data store and the account data store are correlated. In other words, a member's personal data and account data are kept in the respective data stores. A separate mapping data store 306 is used to store the correlation (e.g., a mapping) of the AIDs and PIDs. The mapping data store provides the key for linking account information such as names, addresses, etc., of the individuals to their respective personal information, such as genetic/phenotypic information, medical history, etc. In some embodiments, only persons having administrator status are allowed to access the mapping information. In some embodiments, an automated process is used to receive a query from a researcher or an investigator, verify the account making a query, look up the AID based on the PID or vice versa, and return the result to the verified account.

Data stores 302, 304, and 306 are said to be separate because access to data in each data store is restricted to a specific type of user. A user with a particular assigned role is only allowed to access one of the databases. The data stores may be implemented as separate databases (residing on the same or separate devices), as separate data tables within the same database, or as any other appropriate techniques that provide access control.

In this example, the system is configured to support at least two types of users: researchers and investigators. The researchers, who are in charge of analyzing the data of the studies, have access to personal information data store 302 only. The investigators, who are in charge of coordinating the studies and interfacing with the individuals participating in the studies, have access to account information data store 304 only. In some embodiments, there is also an administrator user type who has access to mapping data store 306 only.

In this example, the researcher can gain access to personal information of individuals in a cohort by logging on to his account. Since he only has access to personal data store 302, he does not have the capability of finding out the real world identities of these individuals since he has no access to their contact information. For example, the researcher has access to a cohort for people with APOE e4 genotype. He is informed that the cohort includes individuals with the PIDs of A2569 (who is male, has no Alzheimer's, but is diabetic and a smoker) and Z3317 (who is female, has Alzheimer's, and is a non-smoker). Since he does not have access to the mapping data store or the account data store, he is unable to find out the real names and contact information of A2569 and Z3317.

In some embodiments, through a manual process conducted by the administrator or an automated secure process performed by the system, the individual's AID is determined based on their PID based on mapping data store 306. In this example, PID A2569 maps to AID NO253, and PID Z3317 maps to AID K9610. The AIDs are passed on to the investigator, who uses the AIDs to look up the individuals' contact information, makes contact with the individuals, signs them up for the study, and administers the study. In the example shown, AID NO253 corresponds to Bob Smith and AID K9610 corresponds to Alice Johnson. Since the investigator has no access to the personal data store or the mapping data store, he would not be able to find out specific genetic, phenotypic, or other health-related information for Alice or Bob through the system automatically without approval by an administrator. In some exceptional cases, the investigator may need to know certain pieces of genetic or phenotypic information in order to do their job. The transfer of such information to the investigator would require special approval by an administrator. In general, neither the researcher, nor the investigator, nor the administrator, can act alone to determine, for example, whether Bob Smith has the APOE e4 gene or is diabetic.

In some embodiments, to further reduce the chance of individuals' real world identity and their personal information being linked and revealed, the personal information data store is programmed such that a response set must comprise at least N individuals, where N is an integer greater than 1 and preferably greater than 2. This way, any attempt at obtaining personal information for a specific individual (such as a query of "does Bob Smith have the APOE e4 gene") will automatically fail because the response data set size is too small.

In some embodiments, the separate data stores are implemented on the same or distinct physical devices. In some embodiments, the data stores are implemented as separate databases with different access privileges for different users, separate tables within the same database with different access privileges for different users, or other access controlled data storage. In various embodiments, access control for different types of users can be implemented using access control settings provided by the database system or the file system, or any other appropriate techniques.

Figure 4:
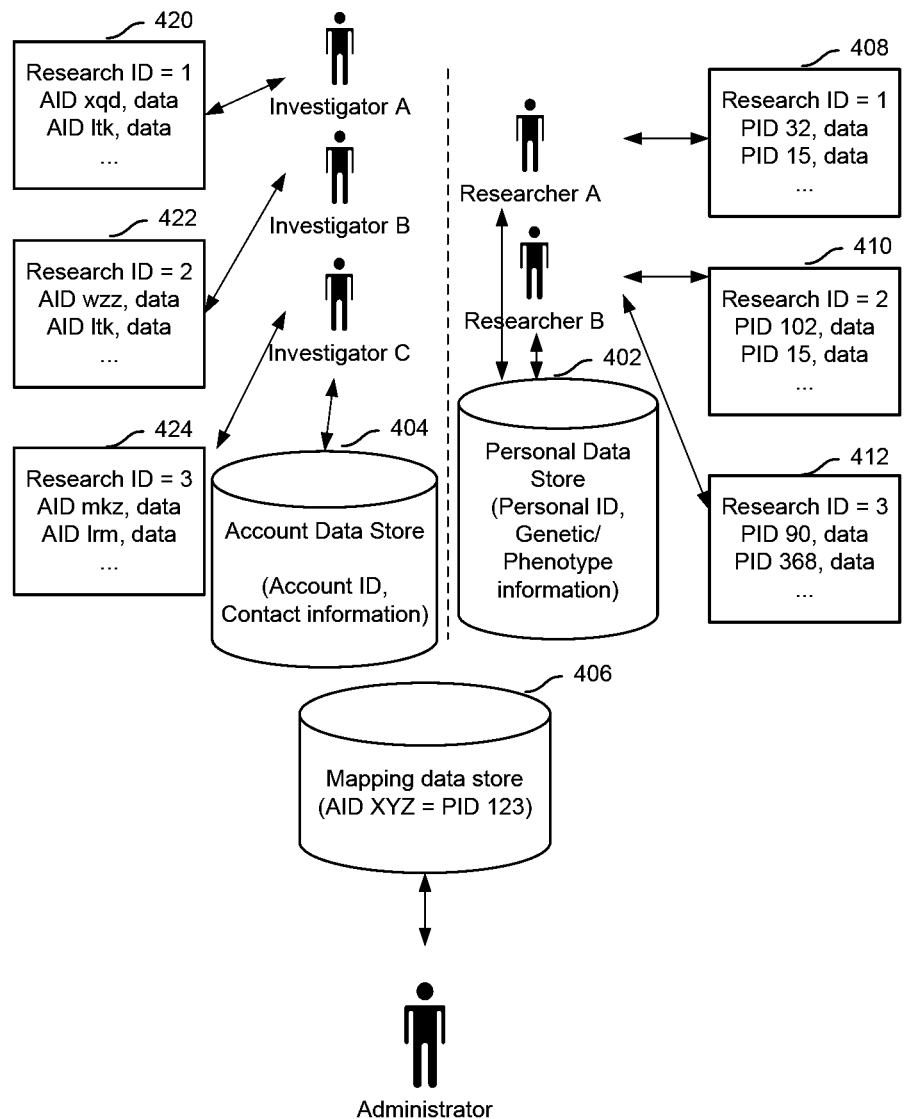
FIG. 4 is a data diagram illustrating the data structures used in an embodiment of a cohort assembling system that supports assembling cohorts based on projects.

In some embodiments, the portal allows multiple projects (also referred to as research studies) to be carried out on the platform, and provides project-based data access control. FIG. 4 is a data diagram illustrating the data structures used in an embodiment of a cohort assembling system that supports assembling cohorts based on projects. In some embodiments, when a cohort for a project is formed, information pertaining to the project is stored. In this example, a researcher or an investigator is assigned to one or more specific projects. The assignment information may be stored in the database or in another location for access control. When an individual becomes a part of a cohort for a project, his/her information becomes associated with the project and is only accessible by the researcher/investigator assigned to the project. As shown, separate tables 408-412 are used for storing PID information specific to a research project. Each table includes an additional research identifier (RID) field (also referred to as a tag) identifying the particular research project, PIDs associated with the personal information of individuals participating in the particular research project, and any related data of the individual pertaining to the research project (e.g., a note regarding the individual with the PID within the context of the research project). Information with the same RID belongs to the same project. The same individual may participate in multiple research projects and therefore be associated with multiple RIDs. For example, the individual with PID 15 participates in research projects 1 and 2.

Project-based access control is implemented to allow different researchers/investigators access to their respective research projects only. A researcher/investigator may be associated with multiple research projects. For example, researcher B is associated with research projects 2 and 3 and therefore is only allowed to access tables 410 and 412, but not 408.

In the example shown, like researchers, investigators are also assigned on a per project basis. Project-based mapping tables 420-424 are used to store AIDs and related data associated with corresponding RIDs. Investigators are given limited access to only the AIDs and related information associated with the research project to which they are assigned.

Figure 5:
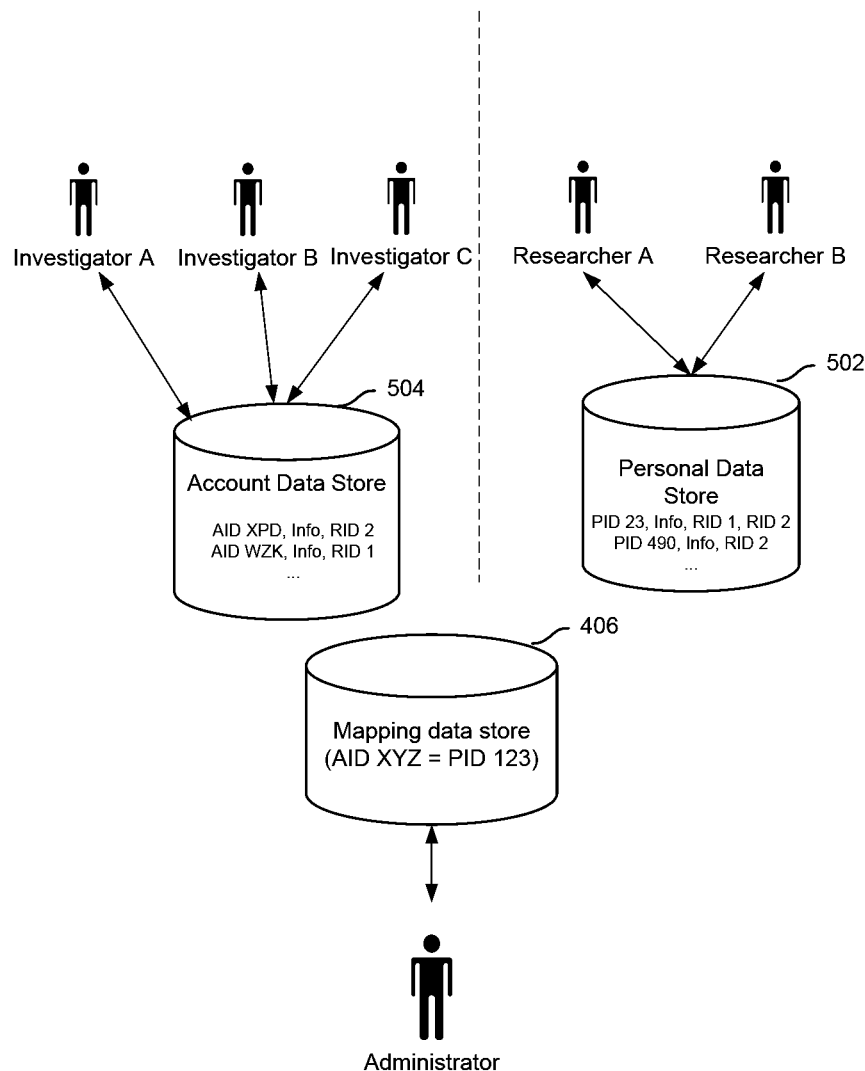
FIG. 5 is a data diagram illustrating the data structures used in another embodiment of a project-based cohort assembling system.

Although research specific information stored in separate tables is shown, any other appropriate data organization schemes may be used. FIG. 5 is a data diagram illustrating the data structures used in another embodiment of a project-based cohort assembling system. In this example, each researcher or investigator is assigned to one or more specific projects. The assignment information may be stored in the database or in another location for access control. Instead of having separate tables for research project-based information, RID(s) associated with each individual is stored in the personal data store and the account data store along with other information to provide data access control. Thus, if researcher A (or investigator A) is assigned to a research project with RID of 1, he is only able to access personal data (or account data) for individuals with RID of 1. In this example, the data stores provide project-based access control by identifying the researcher/investigator and their associated projects, and forming queries restricted to the project identifiers to provide data of individuals participating in the project.

As another example, instead of the account/personal data stores, the RID information can be stored in the mapping data store to control access of data by researchers/investigators. When querying the personal data store/account data store, there is an additional lookup that takes place on the mapping data store based on the RID associated with the researcher/investigator making the query, and only data associated with the particular RID is returned.

In some embodiments, to ensure that users only access information permissible according to their respective assigned roles, the system implements an audit trail to log various activities and may alert the administrator and/or prohibit certain actions if suspicious activities that may lead to data leak occur. For example, designating the same user account as both an investigator and a researcher would allow the same user access to both account information and personal information. Such a designation, therefore, should be prohibited and/or brought to the attention of the administrator.

Figure 6:
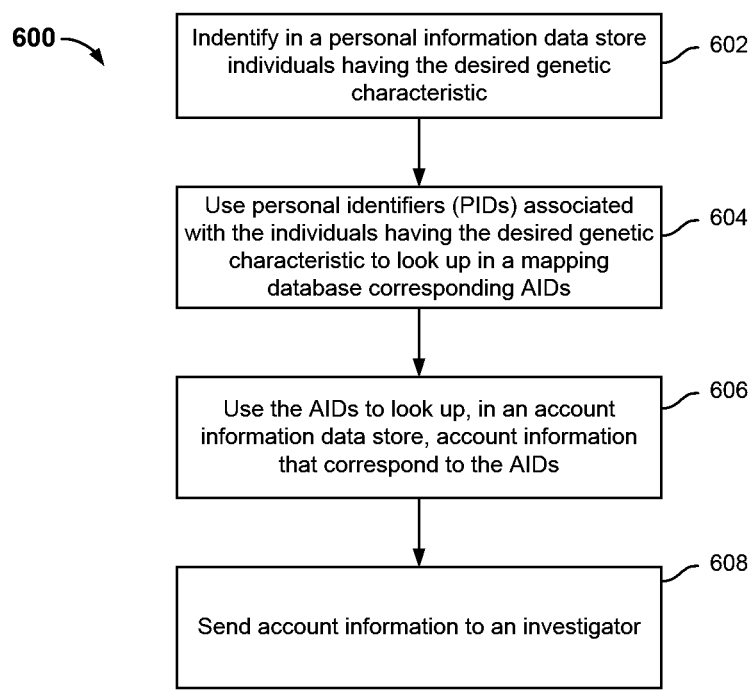
FIG. 6 is a flowchart illustrating an embodiment of a process for deriving a candidate group

FIG. 6 is a flowchart illustrating an embodiment of a process for deriving a candidate group. Process 600 may be used to implement 204 of process 200.

Assume that the desired genetic characteristic for a cohort has been entered into the system by a researcher. At 602, in a personal information data store (e.g., 302), individuals with the desired genetic characteristic are identified as candidates. At 604, the PIDs of the identified individuals are used to look up corresponding AIDs in a mapping data store (e.g., 306). In some embodiments, an automatic look up process is performed based on the PIDs. In some embodiments, the PIDs are sent to an administrator with access to the mapping table to perform a manual lookup. At 606, the AID is used to look up corresponding account information in an account information data store. The look up may be performed automatically based on the AIDs, or manually by an investigator who receives the AIDs from the mapping data store. At 608, the account information (which corresponds to candidate information) is sent to the investigator.

In embodiments that support project-based data access control, in addition, the RID of the project is stored in association with personal/account information of individuals that are selected into the project cohort so that RID-based access control may take place when the researcher/investigator access the stored data at a later point.

In the above examples, cohorts are described to be associated with health-related research. In some embodiments, the cohorts are selected as target groups for education and/or advertising. For example, cohorts that have a particular disease-causing genetic condition may be given information about treatments for the disease.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for assembling a cohort, comprising:
one or more processors configured to:
receive genetic characteristic information pertaining to a desired genetic characteristic;
use the genetic characteristic information to search a data storage comprising information of previously genotyped individuals to derive a candidate group having the desired genetic characteristic, wherein the data storage of previously genotyped individuals includes:
a personal data storage comprising genetic information of the previously genotyped individuals, the genetic information being identified using a first set of anonymized identifiers associated with the previously genotyped individuals;
a separate account data storage comprising contact information associated with the previously genotyped individuals, the contact information being identified using a second set of anonymized identifiers associated with the previously genotyped individuals; and
a separate mapping data storage that maps the first set of anonymized identifiers identifying the genetic information of the previously genotyped individuals to corresponding ones of the second set of anonymized identifiers identifying the contact information of the previously genotyped individuals;
assemble the cohort based at least in part on the candidate group;
in response to a request to gain access to personal information of the cohort by a first user permitted to access genetic information of the previously genotyped individuals, send data pertaining to individuals in the cohort that is obtained from the personal data storage and prevent the first user from accessing data in the separate account data storage; and
in response to a request to gain access to contact information of the cohort by a second user permitted to access contact information of the previously genotyped individuals, send data pertaining to individuals in the cohort that is obtained from the separate account data storage and prevent the second user from accessing data in the personal data storage; and
one or more memories coupled to the one or more processors, configured to provide the one or more processors with instructions.

2. The system of claim 1, wherein the information of the previously genotyped individuals comprises genomic information of the previously genotyped individuals.

3. The system of claim 1, further comprising applying an additional criterion to the candidate group to select members of the cohort that meet the additional criterion.

4. The system of claim 3, wherein the additional criterion is based on additional genetic information.

5. The system of claim 4, wherein the additional genetic information includes relatedness of candidates.

6. The system of claim 4, wherein the additional genetic information includes race.

7. The system of claim 4, wherein the additional genetic information is stored in the database.

8. The system of claim 1, wherein assembling the cohort includes adding relatives of the candidates to the cohort.

9. The system of claim 1, wherein the one or more processors are further configured to return results to a query to the personal data storage or the account data storage only when at least a threshold number of individuals are included in the results, and to indicate a failure when the results include fewer than the threshold number of individuals.

10. The system of claim 1, wherein the one or more processors are further configured to provide an audit trail.

11. The system of claim 1, wherein using the genetic characteristic information to search a data storage comprising information of previously genotyped individuals to derive a candidate group having the desired genetic characteristic includes:
- identifying personal identifiers associated with the candidate group in the personal data storage;
- looking up corresponding account identifiers associated with the candidate group in the mapping data storage; and
- sending account information of the candidate group to the second user with permission to access account information.

12. The system of claim 1, wherein the one or more processors are further configured to store information pertaining to a research project in association with members in the cohort.

13. The system of claim 1, wherein the one or more processors are further configured to store information pertaining to a research project in association with members in the cohort, and provide project-based access control.

14. The system of claim 1, wherein the first set of anonymized identifiers and the second set of anonymized identifiers do not relate to or reveal real world identities of the previously genotyped individuals.

15. A method for assembling a cohort, comprising:
- receiving genetic characteristic information pertaining to a desired genetic characteristic;
  - using the genetic characteristic information to search a data storage comprising information of previously genotyped individuals to derive a candidate group having the desired genetic characteristic, wherein the data storage of previously genotyped individuals includes:
    - a personal data storage comprising genetic information of the previously genotyped individuals, the genetic information being identified using a first set of anonymized identifiers associated with the previously genotyped individuals;
    - a separate account data storage comprising contact information associated with the previously genotyped individuals, the contact information being identified using a second set of anonymized identifiers associated with the previously genotyped individuals; and
    - a separate mapping data storage that maps the first set of anonymized identifiers identifying the genetic information of the previously genotyped individuals to corresponding ones of the second set of anonymized identifiers identifying the contact information of the previously genotyped individuals;
- assembling the cohort based at least in part on the candidate group;
- in response to a request to gain access to personal information of the cohort by a first user permitted to access genetic information of the previously genotyped individuals, sending data pertaining to individuals in the cohort that is obtained from the personal data storage and preventing the first user from accessing data in the separate account data storage; and
- in response to a request to gain access to contact information of the cohort by a second user permitted to access contact information of the previously genotyped individuals, sending data pertaining to individuals in the cohort that is obtained from the separate account data storage and preventing the second user from accessing data in the personal data storage.

16. A computer program product for assembling a cohort, the computer program product being embodied in a non-transitory computer readable storage medium and comprising computer instructions for:
- receiving genetic characteristic information pertaining to a desired genetic characteristic;
  - using the genetic characteristic information to search a data storage comprising information of previously genotyped individuals to derive a candidate group having the desired genetic characteristic; wherein the data storage of previously genotyped individuals includes:
    - a personal data storage comprising genetic information of the previously genotyped individuals, the genetic information being identified using a first set of anonymized identifiers associated with the previously genotyped individuals;
    - a separate account data storage comprising contact information associated with the previously genotyped individuals, the contact information being identified using a second set of anonymized identifiers associated with the previously genotyped individuals; and
    - a separate mapping data storage that maps the first set of anonymized identifiers identifying the genetic information of the previously genotyped individuals to corresponding ones of the second set of anonymized identifiers identifying the contact information of the previously genotyped individuals;
- assembling the cohort based at least in part on the candidate group;
- in response to a request to gain access to personal information of the cohort by a first user permitted to access genetic information of the previously genotyped individuals, sending data pertaining to individuals in the cohort that is obtained from the personal data storage and preventing the first user from accessing data in the separate account data storage;
- in response to a request to gain access to contact information of the cohort by a second user permitted to access contact information of the previously genotyped individuals, sending data pertaining to individuals in the cohort that is obtained from the separate account data storage and preventing the second user from accessing data in the personal data storage.

* * * * *